United States Patent [19]

Pomerantzeff

[11] 4,200,362
[45] Apr. 29, 1980

[54] OPHTHALMOSCOPE WITH UNIFORM ILLUMINATION

[75] Inventor: Oleg Pomerantzeff, Brookline, Mass.

[73] Assignee: Retina Foundation, Boston, Mass.

[21] Appl. No.: 808,181

[22] Filed: Jun. 20, 1977

Related U.S. Application Data

[63] Continuation-in-part of Ser. No. 672,506, Mar. 26, 1976, abandoned, which is a continuation-in-part of Ser. No. 292,150, Sep. 25, 1972, which is a continuation-in-part of Ser. No. 536,879, Dec. 27, 1974, Pat. No. 3,954,329, which is a continuation-in-part of Ser. No. 292,150, , and Ser. No. 512,327, Oct. 4, 1974, Pat. No. 3,944,341.

[51] Int. Cl.² .............................................. A61B 3/10
[52] U.S. Cl. ..................................................... 351/16
[58] Field of Search .................................. 351/6, 7, 16

[56] References Cited

U.S. PATENT DOCUMENTS

| 3,259,039 | 7/1966 | Okajima | 351/7 X |
|---|---|---|---|
| 3,514,193 | 5/1970 | Himmelmann | 351/7 |
| 3,954,329 | 5/1976 | Pomerantzeff | 351/6 X |
| 4,026,638 | 5/1977 | Govignon | 351/7 |

OTHER PUBLICATIONS

Paul R. Lichter, "Transillumination ... Eye," Am. J. of Ophthalmology, vol. 73, No. 6, pp. 927–929 & 931, Jun. 1972.

Primary Examiner—Paul A. Sacher
Attorney, Agent, or Firm—Kenway & Jenney

[57] ABSTRACT

Apparatus for viewing an eye fundus through a contact lens has an illuminating element that illuminates the fundus through the sclera. The illuminating element includes at least one fiber optic bundle with an exit facet for placement contiguous with the sclera, generally through whatever thickness of occular conjunctiva is present. The apparatus also has an optical mask system which masks the image of the fundus portion most intensely illuminated by the fiber optic exit facet to control over-illumination of that fundus portion.

38 Claims, 18 Drawing Figures

OPHTHALMOSCOPE WITH UNIFORM ILLUMINATION

CROSS REFERENCE TO RELATED APPLICATIONS

This application is a continuation-in-part of my co-pending application Ser. No. 672,506 filed Mar. 26, 1976 now abandoned for "Ophthalmoscope With Uniform Illumination". That application is a continuation-in-part of my co-pending application Ser. No. 292,150 filed Sept. 25, 1972 entitled "Wide-Angle Ophthalmoscope"; and of my application Ser. No. 536,879 filed Dec. 27, 1974 entitled "Wide-Angle Ophthalmoscope Employing Transillumination", and now U.S. Pat. No. 3,954,329, which is a continuation-in-part of said application Ser. No. 292,150, and of application Ser. No. 512,327 filed Oct. 4, 1974 entitled "Wide-Angle Ophthalmoscope And Fundus Camera", and now U.S. Pat. No. 3,944,341; all of which are assigned to the assignee hereof. Filed concurrently with application Ser. No. 672,506 is another patent application Ser. No. 670,701 directed to an "Illumination System For Ophthalmoscope"; now U.S. Pat. No. 4,061,423.

BACKGROUND OF THE INVENTION

This invention relates to an ophthalmoscope, i.e., an instrument for viewing the interior of the eye. More particularly, the invention provides a wide-angle ophthalmoscope which achieves more uniformly illuminated imaging of the eye fundus than heretofore possible.

The invention thus provides a wide-angle ophthalmoscope having a superior uniformity of image intensity at the ophthalmoscope viewing location, as compared to prior devices of this kind. Due to these and other advantages set forth below, an ophthalmoscope embodying the invention enables superior viewing of the entire retina, and photographing it, in a single image with a single placement of the instrument.

My previous patents and patent applications, noted above, describe wide-angle ophthalmoscopes having improved constructions for both illumination through the crystalline lens and transillumination through the sclera of the patient. With the first type of illumination there is often a noticeable diminution of illumination at the posterior pole of the fundus as well as the requirement for significant dilation of the patient's pupil; with the second there is an intensely bright spot on the image corresponding to the fundus portion adjacent the sclera location where transillumination occurs.

Accordingly, it is an object of this invention to provide a wide angle fundus-viewing instrument in which the optical intensity of the fundus image, as seen from the viewing location, is more uniform than in prior devices of this kind.

A further object is to provide improvements in a transillumination type ophthalmoscope that yield such improved image uniformity and that can be provided as add-on features to existing ophthalmoscopes of this type.

It is also an object of this invention to provide a wide-angle ophthalmic instrument using illumination applied through the eye sclera and which provides an image having relatively uniform brightness. It is a further object to provide such an instrument capable of providing such uniform image brightness with subjects having eyes of different geometries, i.e. different sizes and shapes.

Another object of the invention is to provide an ophthalmic device of the above character which is of relatively simple and low cost construction, and which is relatively easy to operate.

Other objects of the invention will in part be obvious and will in part appear hereinafter.

BRIEF DESCRIPTION OF DRAWINGS

For a fuller understanding of the nature and objects of the invention, reference should be made to the following detailed description and the accompanying drawings, in which.

SUMMARY OF THE INVENTION

The invention stems from the finding that the illumination of a retina through the sclera, for ophthalmologic examination, can be made more apparently uniform at the instrument output than occurs with reliance only on sclera diffusion of light. In the new instrument, optical mask means effectively reduce fundus image intensity at over-illuminated locations (i.e. the locations corresponding to the exit fact of the light source).

In the practice of the invention, the transillumination is preferably directed through a narrow region of the sclera termed the pars plana. This region lies in a generally annular area between the ciliary body and the ora cerrata.

Examination of an eye with transillumination through the pars plana and with appropriate optical output masking according to the present invention can provide a field of view and an observable field of 160° from the nodal point, all of which is imaged with superior apparent uniformity of illumination. Hence, this image of the field can be more readily examined by an observer and/or photographed, or otherwise recorded, as a single scene or frame. Further, the uniform brightness of the image enhances the observation of fine structures and other detail.

A mask system according to the invention has at least one optical mask member located in selected optical alignment with the optical axis of the ophthalmic device. The mask member reduces the brightness of the fundus image at a region of the image corresponding to a location on the fundus where applied illumination enters the eye through the sclera. The mask member preferably is disk-like and has a selected opacity configuration. In one embodiment the mask member is totally opaque with a contoured periphery; in another it has regions of different opacity. The mask member generally lies in a plane transverse to the optical axis and can be reciprocated into and out of the fundus image to provide the desired masking. Alternatively, the mask member can be rotated about an axis parallel to the optical axis. The mask member also can be adjustably moved to match the geometry of the eye being examined, and then either moved as above, or maintained stationary, during viewing for examination and/or recording.

The invention accordingly comprises the features of construction, combination of elements, and arrangement of parts exemplified in the constructions hereinafter set forth, and the several steps effected thereby, and the scope of the invention is indicated in the claims.

DESCRIPTION OF ILLUSTRATED EMBODIMENTS

Figure 1:
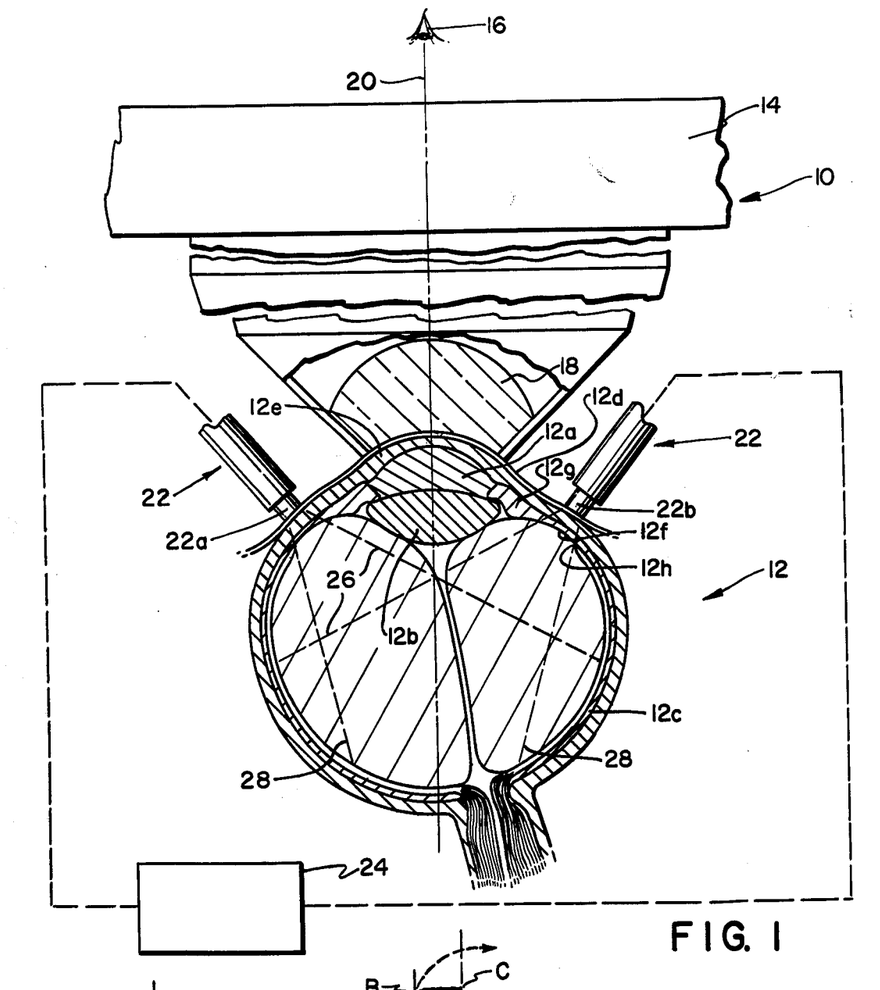
FIG. 1 is a schematic, horizontal plan view of a trans-illumination type ophthalmoscope operatively positioned on an eye.

FIG. 1 shows a wide-angle ophthalmoscope 10 according to the invention operatively disposed contacting a human eye indicated generally at 12. The ophthalmoscope includes an optical mask system housing 14 in front of a viewing or recording device 16, which can include an observer's eye, a camera, or other optical viewing or recording equipment. The ophthalmoscope has a contact lens 18 that images the eye fundus outside the eye. That is, the contact lens 18 enables an exterior viewer to observe up to essentially a 160° solid angle of the eye fundus through the pupil 12a and crystalline lens 12b of the eye.

The ophthalmoscope has a fundus illumination system 22, illustrated in the form of bundles 22a and 22b of optical fibers, which directs light from a source 24 into the interior of the eyeball through the sclera 12c, and whatever thickness of the conjunctiva 12d which is present. The sclera and adjacent layers of the eye structure diffuse the light that the lamp element 22 projects. Hence, the resultant illumination within the eyeball is scattered throughout the fundus. The two bundles 22a and 22b preferably are disposed on the horizontal sides of the pupil in the access space normally available on an eye, i.e. the placement of one is temporal and of the other is nasal. Where desired, of course, one or more bundles can be placed elsewhere on the eyeball, with evident related changes in the optical mask system discussed below. (The ophthalmoscope can include a second lamp element formed by optical fibers disposed in a conical array around the contact lens 18, in the manner disclosed in my prior patents and patent applications noted above.)

In view of the foregoing, it should be understood that when in use, the ophthalmoscope is centered on the eye 12 and hence the lens 18 is located on the cornea 12e optically aligned with the crystalline lens 12b along an optical axis 20. Each bundle 22a, 22b of the lamp element 22 is generally normal to the eyeball and is disposed at the sclera 12c. Further, each bundle is located at the pars plana 12f, which is the annular portion of the sclera between the ciliary body 12g and the ora cerrata 12h. As previously noted, the optical transmission of the sclera and the adjacent layers at the ora cerrata is relatively high in the regions of the spectrum that are used, due to the small thickness of optically-absorbing material there, as contrasted with adjacent regions.

The ophthalmoscope contact lens 18, when in contact with an eye cornea as illustrated, increases the power of the optical system of the eye being examined and brings the image of the fundus from infinity to a finite distance in front of the eye. For this purpose, the lens has a concavo-convex configuration with generally frusto-conical sides. The lens construction may be as described in the above-mentioned U.S. application Ser. No. 536,879.

Each fiber optic bundle 22a, 22b of the lamp element 22, as already noted, is configured to be disposed on the eye to illuminate the fundus through the sclera at the region of maximum optical transparency, i.e. at the pars plana. There preferably are two bundles 22a and 22b as illustrated, one located temporally and the other in a nasal location. Each bundle contacts the sclera at a spacing generally between ten and seventeen millimeters from the axis 20 in order to engage the pars plana. The exact location of the bundles against the eyeball for optimum illumination will, of course, vary depending on the size of the eyeball being examined. A construction in which each bundle has a diameter of five to six millimeters at its engagement with the eyeball, and in which the bundle engages the eyeball at around fourteen millimeters from the central axis 20, suffices for most instances. With this arrangement, light from the two bundles 22a and 22b appears as two bright spots on the inner surface of the bulb of the eye, and illuminates the posterior segment of the bulb.

FIG. 1 shows that the resultant aperture of direct illumination (i.e. excluding diffusion and scattering) from each bundle 22a and 22b is within a solid angle bounded by the rays 26 and 28. This aperture of direct illumination typically is a 48° solid angle. However, as noted, there is significant diffusion of the illumination from the lamp element 22 in passing into the interior of the eyeball so that the illumination from each bundle is scattered far beyond the region of direct illumination. This scattering generally is considered desirable, for it enhances illumination over the entire observable field of the fundus.

Figure 2:
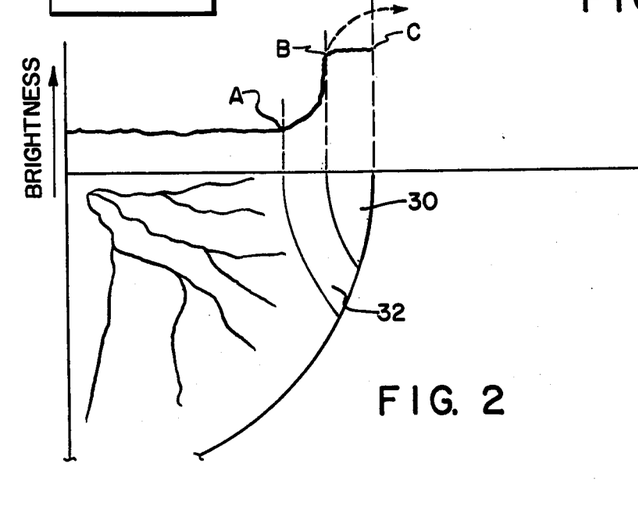
FIG. 2 is a schematic illustration of a portion of the fundus image produced by the ophthalmoscope of FIG. 1.

Referring to FIG. 2, the lower portion is an illustration of a quadrant of the fundus image produced by an ophthalmoscope constructed in accordance with the teaching, for example, of the above-mentioned U.S. application Ser. No. 536,879. A region 30 at the lateral periphery of the image is very bright owing to the positioning of the fiber optic bundles 22a and 22b adjacent the corresponding fundus portions. That is, the image has a region 30 of bright illumination or "flare" at the site of each bundle 22a and 22b. According to the present invention, I have found that in each region 30 there is typically a complete saturation of the photographic film upon which the fundus image is recorded, e.g. when recording device 16 is a camera. Referring to the upper portion of FIG. 2, it shows a graph of illumination intensity as a function of location on a diameter across the fundus image shown in the lower portion of FIG. 2. The solid line of the graph is representative of the illumination intensity at various regions of the fundus and was obtained by measuring degrees of exposure of the photographic film at corresponding locations of the fundus image. As is evident from FIG. 2, the brightness is substantially uniform from the center of the image out to a location, indicated at A, that corresponds to the beginning of a region 32 surrounding the bright region 30 of the fundus image. In this region 32, as is evident from the graph, the level of light illuminating the fundus portion increases with increased proximity to region 30. In the region 30, however, measurements from the photographic film would indicate a uniform brightness (see the graph portion between points B and C), although at a much higher level than the uniform brightness at central portions of the fundus, i.e. to the left of point A.

I have realized, however, that this apparent uniformity of illumination in the region 30 is actually the result of saturation of exposure of the photographic film and that there is a real increase in the level of illumination on the fundus in this portion as indicated by the broken line segment of the graph in FIG. 2. It is the analysis of these increased levels of brightness at peripheral portions of the fundus, as well as an implementation of an ophthalmoscope that corrects for this situation, that form the basis of the present invention.

Figures 3, 4:
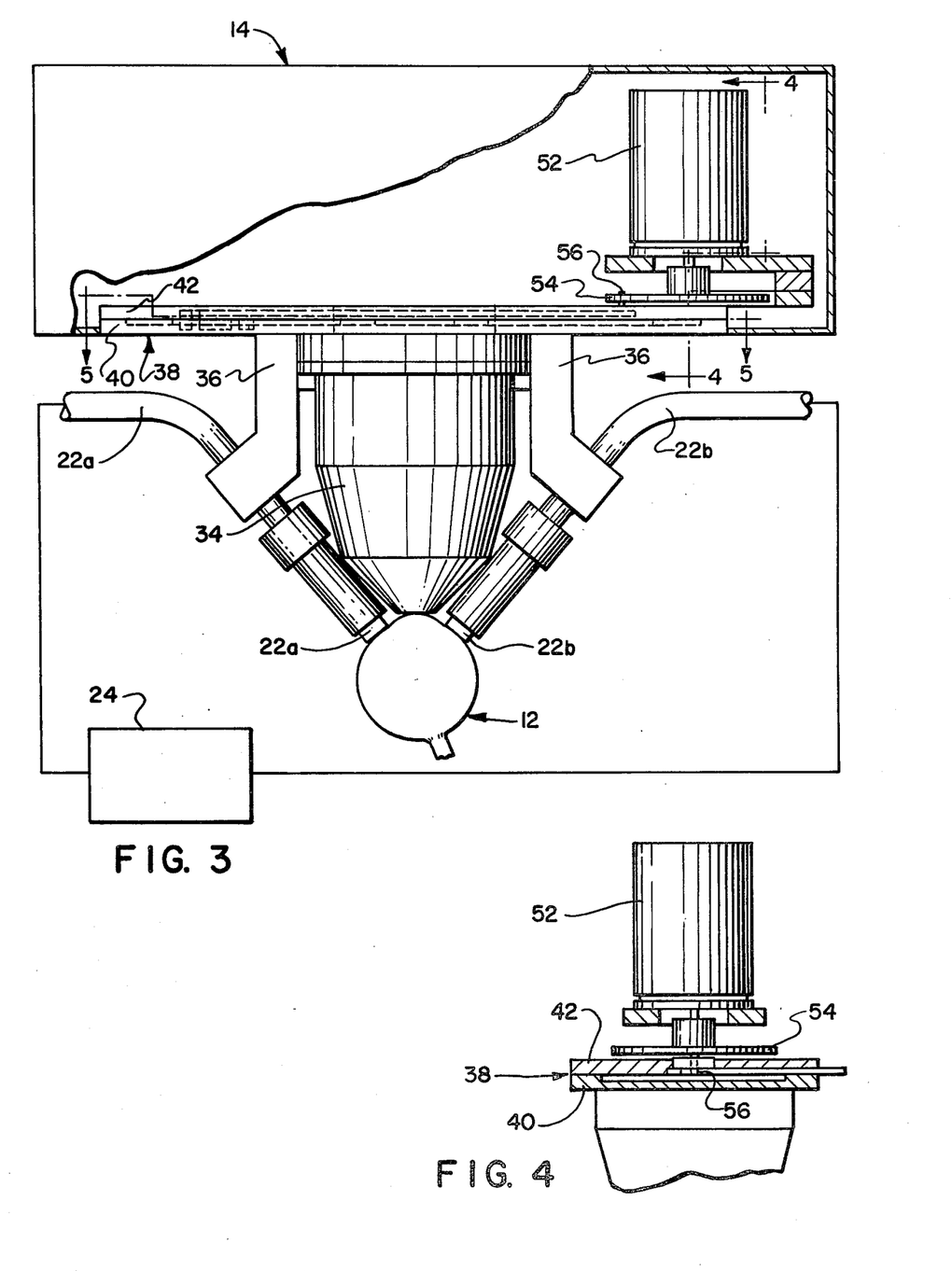
FIG. 3 is a partially broken away view, similar to FIG. 1, of a modified ophthalmoscope embodying features of the present invention.
FIG. 4 is a view taken at line 4—4 of FIG. 3.

FIG. 3 is an illustration of one ophthalmoscope constructed in accordance with the present invention and showing somewhat more detail than FIG. 1. Thus, the optical elements are supported within a housing 34 that is mounted on a larger housing 37 which encloses an optical mask system. Brackets 36 mounted on the housing 37 support the fiber optic bundles 22a and 22b at locations somewhat spaced (e.g. one and one-half inches) from the bundle end faces that contact the patient's eye.

In view of my findings summarized above with reference to FIG. 2, I have realized the desirability of providing in the ophthalmoscope an optical mask system to mask the portions of the optical image which correspond to the regions 30 and 32 of FIG. 2 to compensate for the excessive illumination of the fundus at the corresponding regions thereof. The mask system of FIG. 3 provides this operation in a timed sequence. This optical mask system is described with reference to the broken away portion of housing 37 in FIG. 3 and with reference to FIGS. 4 and 5.

The illustrated optical mask arrangement includes a frame 38 formed with front and rear frame members 40 and 42. Each frame member has a central circular opening 44 that is aligned with the optical axis 20 (see FIG. 1) of the ophthalmoscope's optical system and that defines the aperture of the image transmitted by the ophthalmoscope to the observer, camera, etc. (The opening 44 thus corresponds to a spatially-displaced, full image of the fundus, a quadrant of which is illustrated in FIG. 2). The frame member 42 forms a rectangular recess 46 within which a pair of mask members 48, 48 is slidably supported.

Each mask member 48 includes a curved lobe 50 directed toward the optical axis 20 of the system and having curvature chosen substantially to match the curvatures of the regions 30 and 32 illustrated in FIG. 2. Each mask member 48 is slidable within the recess 46 between a first position (shown in FIG. 5 with broken lines) in which each lobe 50 overlaps the opening 44 to mask an area substantially equal to the combined areas of regions 30 and 32 in FIG. 2, and a second position (shown with solid lines) in which the lobes 50 are fully retracted so as to not overlap the openings 44 at all. Extreme precision in the size and shape of each lobe 50 is not essential since any empirical determination of the regions 30 and 32 of FIG. 2 includes an inherent degree of imprecision and, also, since those regions, are, in part, determined by the physical characteristics of the eyes of individual patients. In a presently preferred embodiment illustrated, each lobe 50 is a portion of a circle having a radius of 0.71 inch and each lobe projects from the adjacent straight edge 51 of the mask member 48 by a distance of 0.39 inch.

The movement of the mask members 48 between their respective two positions is produced by a precision stepping motor 52 that drives a rotary cam 54, which, in turn, drives a linkage connected to the mask members 48. The cam 54 is a rotary cam wheel or disk coaxial with the drive shaft of stepping motor 52 and includes a cam groove 58 that receives a pin 56 secured to the linkage. As discussed below, according to the present invention it has been realized that a very rapid movement of the mask lobes 50 to mask the region 30 illustrated in FIG. 2 is desirable, and a relatively slower advance of the lobe 50 into the region 32, and any subsequent retraction therefrom, is also desirable. In the illustrated embodiment, the cam 54 has a groove 58 shaped to achieve this type of motion of the mask members. In that embodiment the circumferential extent of the groove is 180° and its total radial extent is 0.354 inch. The groove is cut, however, such that one-half of that radial motion (i.e. 0.177 inch) occurs in the first 18° of rotation of the cam 54 (i.e. the first one-tenth of the total time of rotation) and the remaining 0.177 inch of radial movement occurs in the remaining 162° of rotation. It may be preferable to start operation with the mask lobes fully projected, i.e. in the aforementioned first position, in which case the cycle starts with 162° of cam rotation retracting the lobe slowly, followed by rapid retraction during the next 18° of rotation, rapid initial return and slow final return to the initial position.

Figures 5, 6, 7B:
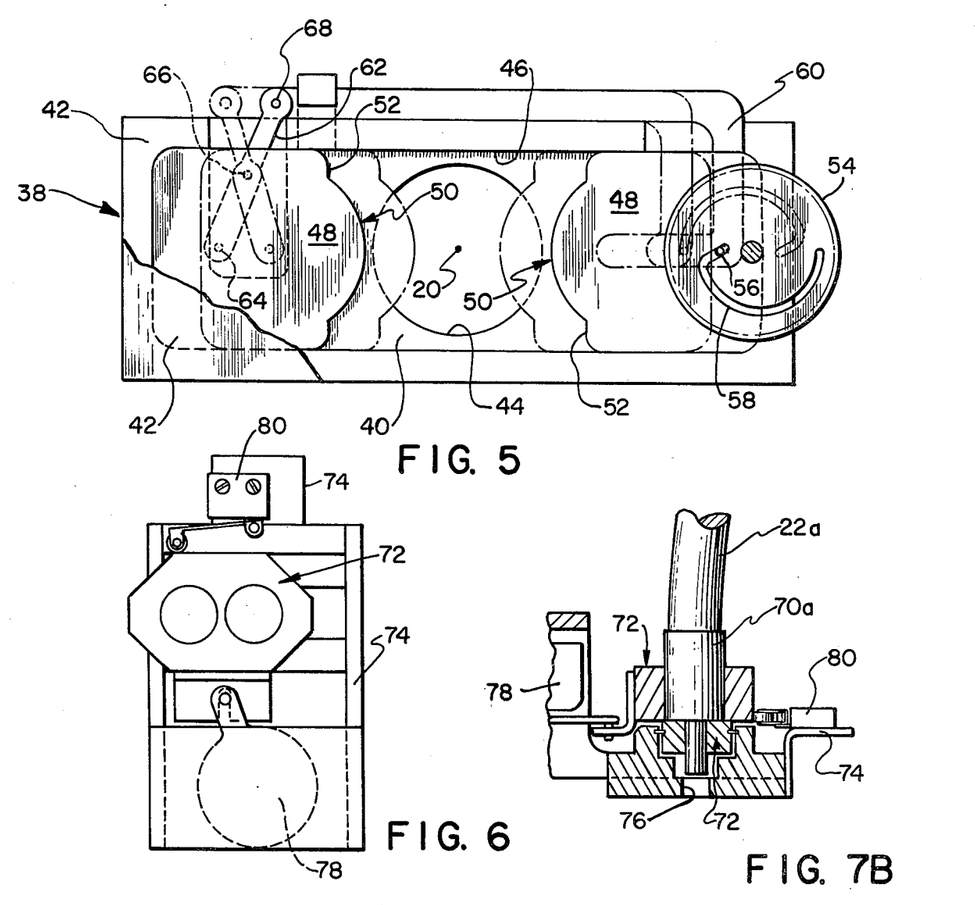
FIG. 5 is a front elevation view of an optical mask system employed in the ophthalmoscope of FIG. 3.
FIG. 6 illustrates a light source arrangement for the ophthalmoscope of FIG. 3.
FIGS. 7A and 7B are section views of the arrangement of FIG. 6.

The pin 56 that engages the groove in the cam 54 is a projection of a pin 56 securing a linkage arm 60 to the mask member 48 closest to the cam. Referring in particular to FIG. 5, this construction causes the right-to-left and left-to-right movement of the mask member 48 on the right hand side of the frame 38, but in a non-linear manner as desired. The linkage arm 60 is pivotally connected to a lever arm 62 itself pivotally connected, as at 64, to the left side mask member 48. A center pivot pin 66 for the lever arm 62 is fixed to the frame member 42 and causes a lateral movement of a pivot point 68 (that defines the connection between the linkage arm 60 and the lever arm 62) to be translated into an opposite lateral movement of the pivot point 64, and thus of the left side mask 48. With this arrangement, the two mask lobes 50 can be simultaneously driven into a masking relationship with respect to the openings 44 (as shown with broken lines in FIG. 5), and simultaneously retracted to a non-masking position.

Turning now to a discussion of the light source (shown schematically in FIG. 3 with reference number 24), it will be appreciated by those skilled in the art, from the discussion in the above-mentioned U.S. application Ser. No. 536,879, that, when transillumination through the sclera is used, two entry points of light (i.e.

temporal and nasal) are preferably employed to assure substantial uniformity of illumination over a major portion of the fundus to be viewed. It is for this reason that there are two bundles 22a and 22b of fiber optics illustrated in FIGS. 1 and 3. The bundles 22a and 22b, of course, simply transmit light received at an input end to an exit facet placed adjacent the sclera. Naturally there are a variety of ways of providing light input to those bundles. For example, independent light sources can be employed for directing an intense beam of light onto the input end of each bundle; or a single light source can be directed upon the input end of a large collection of optical fibers, which is then separated into the two bundles 22a and 22b; etc.

Another alternative will be described with reference to FIGS. 6, 7A and 7B. This illustrated arrangement is particularly suitable for adapting the features of the present invention to existing ophthalmoscopes (such as those constructed in accordance with the cross-referenced patent applications mentioned above) which have but a single light source with a collimated output of limited diameter.

Figure 7A:
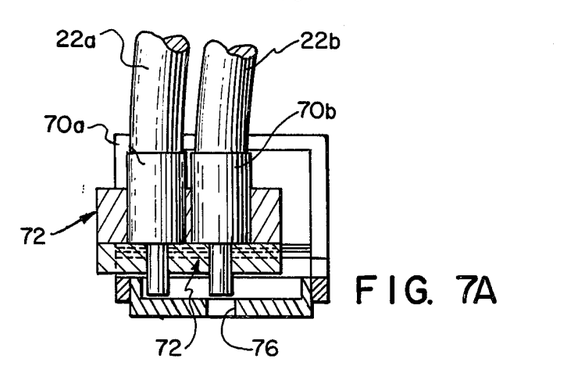

The general arrangement illustrated in FIGS. 6, 7A and 7B is to have end pieces 70a, 70b of the fiber optic bundles 22a, 22b supported in a shuttle 72 that is slidable, relative to the single light source, in a frame 74. Any conventional stop arrangement can be provided for the shuttle to define two shuttle positions. In each of those positions, one of the end pieces 70a, 70b is aligned with an opening 76 that admits light from the ultimate light source. The shuttle is spring loaded toward one of those two positions, and can be driven, against the influence of the biasing spring, by a solenoid 78 to the other of those positions. A microswitch 80, mounted on the frame 74, is positioned to be closed by the shuttle only when in the shuttle position defined by the activated solenoid 78.

While this arrangement requires sequential separate illuminations of the eye fundus employing the bundles 22a and 22b, it is desirable as being compatible with existing ophthalmoscopes. In terms of viewing ease, the sequential illuminations are inconsequential when, as is common, the ophthalmoscope is employed in conjunction with a camera to photograph an image of the fundus. With the camera shutter open the entire time, the two brief illuminations supplied by the bundles 22a and 22b are essentially two "flashes" of a camera flash system, operating while the camera shutter is open, and illuminating a motionless subject in an otherwise dark environment.

Figure 8:
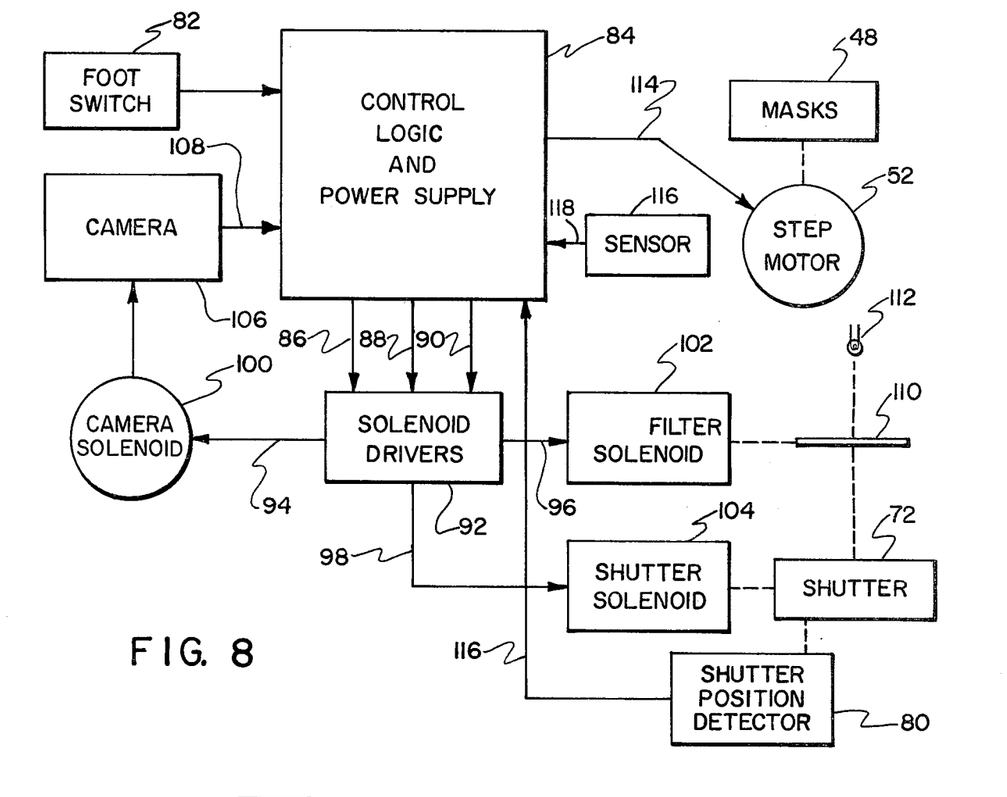
FIGS. 8 and 9 are logic and timing diagrams respectively illustrating the interaction of elements of the ophthalmoscope of FIG. 3.
Figure 9:
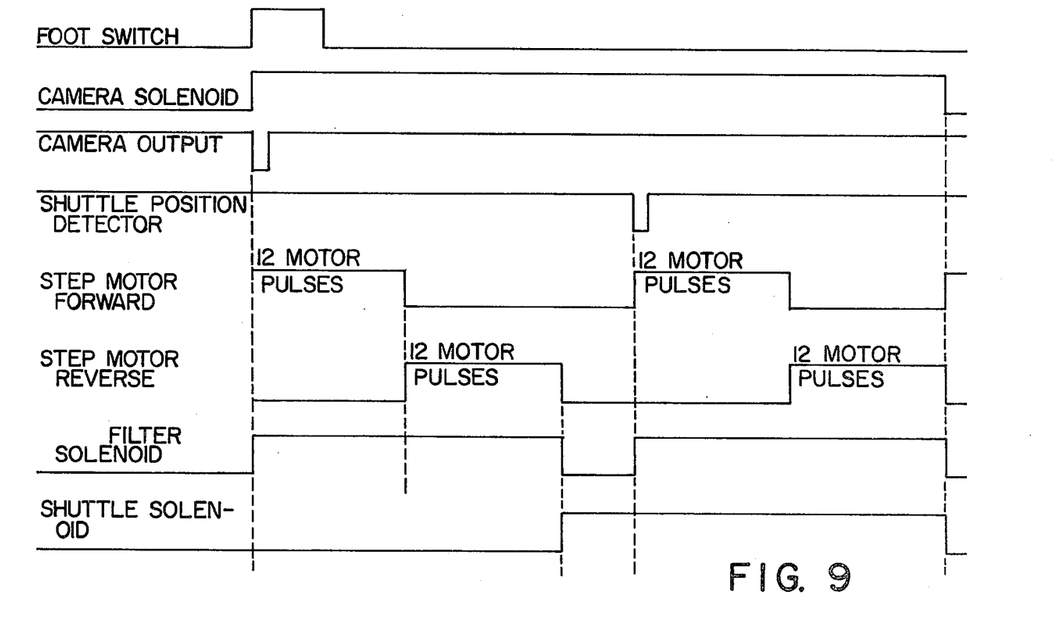

Because, as mentioned above, it is desirable to move the masks through a full cycle, e.g. from a nonobscuring position to a fully obscuring position and back again during each illumination, it will be appreciated that with the lighting arrangement just described two cycles of the optical mask system are preferred for each full observation, photograph, etc. of the fundus. The logic diagram of FIG. 8 and the timing diagram of FIG. 9 illustrate one preferred system for achieving the double illumination, the double masking, and the appropriate timing of all steps in the full sequence of use of the ophthalmoscope.

As described in the previous patent applications referenced above, the ophthalmoscope operator initially positions the contact lens 18 and the fiber optic bundles 22a and 22b in contact with the patient's eye, as illustrated in FIG. 1. The sequence of operation of the instrument, with a camera supported and positioned to receive light transmitted through the openings 44 shown in FIG. 5, may be described with reference to FIGS. 8 and 9. Preferably the sequence of operation is initiated with a foot switch 82 that can be depressed by the operator. The closing of the switch 82 is the initial input to a control logic and power supply unit 84 which, as will be appreciated by those skilled in logic design, can be conventionally constructed to accomplish the functions to be described. Major outputs from the unit 84 are signals appearing on output lines 86, 88 and 90 that are delivered to three solenoid drivers, indicated schematically at 92. The solenoid drivers are operative, upon receiving a corresponding input signal, to deliver an output signal on lines 94, 96 and 98 for driving, respectively, camera solenoid 100, light source filter solenoid 102, and shuttle solenoid 104. As is evident from FIG. 9, the initial action of the unit 84, upon depression of the foot switch 82, is to produce output signals that activate the camera solenoid 100 and the filter solenoid 102. The camera solenoid is connected to open the shutter of the camera 106. As is indicated by lead 108, a signal responsive to the shutter-open condition of the camera 106 is transmitted to the unit 84. This is also indicated in FIG. 9 by the signal in the "camera output" sequence.

Simultaneous with the opening of the camera shutter, the light source filter solenoid 102 drives a filter 110 from the optical path between the ultimate light source 112 and the shuttle 72. The removal of the filter 110 from the light path causes a more intense beam of light to be transmitted through the bundle 22a or 22b for illuminating the fundus of the patient. Because the filter 110 is removed from the light path for short periods of time (i.e. fractions of a second), the action of the filter 110 is analogous to that of a conventional "flash unit" for a conventional camera.

Following the actuation of the camera and filter solenoids 100 and 102, the camera output 108 causes the unit 84 to generate a sequence of twelve uniform pulses delivered on output line 114 for driving the stepping motor 52 twelve steps in a forward direction. After twelve such pulses, the pulse train continues, but with pulses causing the motor to step in the reverse direction for twelve steps. As is evident from FIG. 9, the pulse train is interrupted after the second twelve pulses.

This dual series of twelve motor stepping pulses causes the cam and linkage arrangement described above in relation with FIGS. 3, 4 and 5 to drive the mask elements 48 from a position in which the lobes 50 are non-interfering, to the fully masking position, and back to the original position. Simultaneous with the cessation of the last pulse of the train of twenty-four pulses, the unit 84 causes deactivation of the filter solenoid 102 and the attendant re-insertion of the filter 110 into the light path, thereby avoiding exposure of the photographic film from the intense light at a time when the masking system is not in operation. Also upon cessation of the twenty-fourth pulse, the unit 84 activates the shuttle solenoid 104 causing the shuttle 72 to shift from its first to its second position, so that the fiber optic bundle 22b is now aligned with the light source 112. FIG. 9 illustrates a slight delay in further action owing to the time delay in the mechanical movement of the shuttle.

When the shuttle has reached its second position, however, the shuttle position detector 80 (i.e. the microswitch) delivers an output signal on lead 116, which is indicated schematically in FIG. 9, to the unit 84. This shuttle position detector output causes the unit 84 to initiate a second sequence of twelve forward motor stepping pulses, followed by twelve reverse motor stepping pulses, all applied to line 114 leading to the stepping motor 52. Silmultaneous with the initiation of the first pulse of that second sequence, a signal is generated to cause the filter solenoid 102 to once again remove the filter 110 from the light path. Termination of that signal to the solenoid 102, and consequent re-insertion of the filter 110 into the light path, occurs with the final pulse of the twenty-four pulse series delivered to the stepping motor 52. The filter 110 is therefore removed from the light path only during the sequence of twenty-four pulses which occur during the second exposure of the fundus (i.e. the exposure produced by light delivered through bundle 22b), just as it was with the first exposure. Termination of the second twenty-four pulse train also causes deactivation of the camera solenoid 100 (thereby closing the camera shutter) and deactivation of the filter solenoid 102 and shuttle solenoid 104. Deactivation of these latter solenoids permits the filter 110 and the shuttle 80 to return to their original positions, typically under the influence of biasing springs.

As is evident from the preceding discussion, it is important that the stepping motor 52 and the attached cam member 54 be properly "zeroed" prior to the commencement of an operating sequence of the ophthalmoscope. As a precaution, therefore, a sensor 117 (e.g. a photocell positioned to sense the "zero" position of the cam) can be employed to determine whether or not the stepping motor 52 is at its "zero" orientation. The signal produced by sensor 117 is delivered by a lead 118 to the unit 84. In one preferred arrangement, the unit 84 has an indicator (e.g. a light) on an exposed panel to indicate when the stepping motor is in the zero orientation and when it is removed from that orientation. An associated manually-operated switch can be provided to deliver an uncounted sequence of stepping pulses to the motor 52 when the switch actuator is depressed. With this arrangement, of course, it is a simple matter for the operator of the equipment to zero the stepping motor, prior to initiation of a cycle of operation of the equipment, by simply depressing the switch actuator on the unit 84 until the indicator is in the appropriate condition (e.g. light on or off as the case may be).

It will be understood by those skilled in the art that the sequence of operation of the ophthalmoscope, and an attached interacting camera, is typically quite brief. For example, the total exposure time (i.e. the four twelve-pulse sequences of stepping motor pulses) will typically be no more than one-eighth of a second in duration. As is clear from FIG. 9, with such an exposure time, the total sequence of operation will be only slightly more than an eighth of a second. As will be appreciated by those skilled in the art, the exposure time can be easily adjusted in various ways. One convenient way is to employ a clock (from which the stepping motor pulse sequences are delivered) that has a variable period.

As will also be apparent to those skilled in the art, the shuttle arrangement and the second full sequence of stepping motor operation evident from FIG. 9 could be eliminated by providing for the input of light simultaneously to both fiber optic bundles 22a and 22b. With both bundles illuminating the eye simultaneously, only a single cycle of mask reciprocation is required, and the fundus receives in one-half the time the same level of illumination it receives with the illustrated embodiment operating according to FIG. 9. As mentioned above, however, the light sources tend to be quite expensive so that the cost of the shuttle arrangement, and the additional control logic required, usually will be less than the cost of a second light source. Additionally, certain commercially available ophthalmoscopes are constructed with a single light source and, thus, the described arrangement can be provided in the form of an attachment to be used with existing ophthalmoscopes.

For clarity of description the invention is described in terms of an ophthalmoscope. As noted above, this term is used herein with reference to any device for examining (including recording) an eye fundus. Hence the device 10 illustrated and described herein can be part of a fundus camera, or of another instrument which is used for viewing, recording or otherwise examining an eye fundus.

Figure 10:
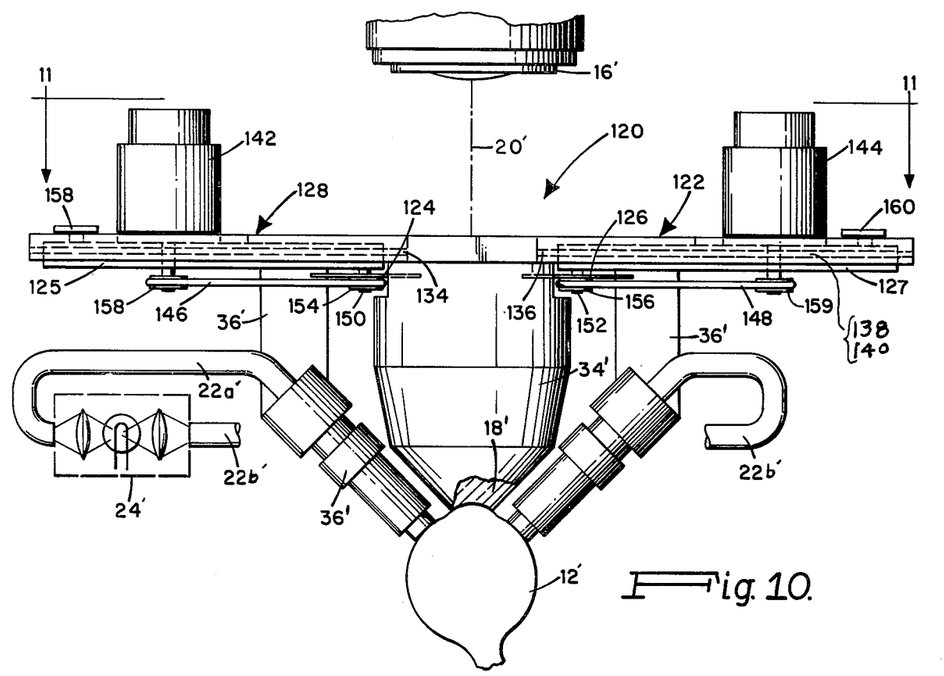
FIG. 10 is a horizontal plan view similar to FIG. 1 of another ophthalmoscope embodying features of the invention.
Figure 11:
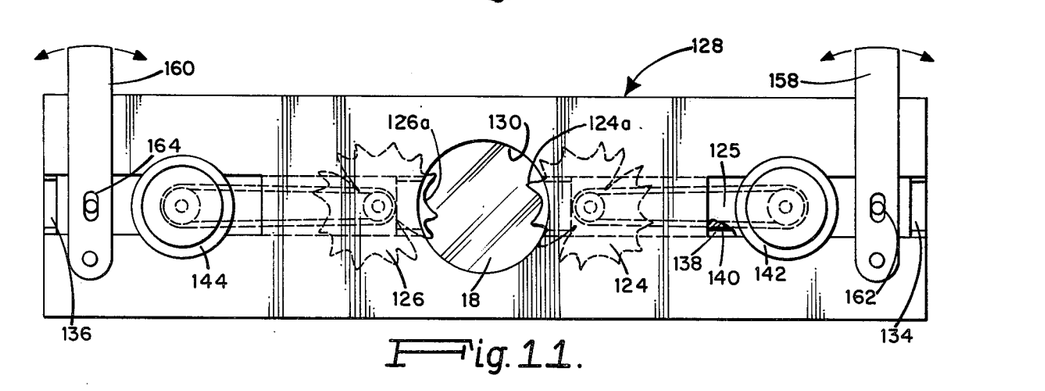
FIG. 11 is an elevation view partly broken away of the ophthalmoscope of FIG. 10 and taken along line 11—11 therein.

FIGS. 10 and 11 show an ophthalmoscope 120 according to another embodiment of the invention which uses rotating masks, rather than reciprocating masks as hereinabove. The rotating mask motion can avoid the need to synchronize the masking with other operations. The ophthalmoscope 120 thus is simple to operate and relatively low in cost, yet provides a wide-angle fundus image that is essentially free of bright spots or other significant nonuniformities in apparent illumination due to light applied through the sclera.

The illustrated rotating mask ophthalmoscope 120 is largely similar to the FIG. 1 ophthalmoscope 10 except for a mask system 122. Accordingly, elements of the ophthalmoscope 120 corresponding to those in FIGS. 1 through 9 bear the same reference numerals except with a superscript prime, for example the ophthalmoscope 120 employs a contact lens 18'. The mask system 122 of the ophthalmoscope 120 employs a pair of disk-like and typically identical masks 124, 126 rotatably mounted on a support casing 128. The casing 128 typically is mounted on a base or stand (not shown) in front of the face of the subject with the axis 20' of the ophthalmoscope aligned with the eye 12' being examined. The casing carries the housing 34' of the contact lens 18' and other optical elements, and mounts brackets 36', 36' which support fiber optic bundles 22a' and 22b' of a fundus illuminating system 22'. A circular opening 130 in the casing is in optical alignment along the axis 20' with the optical elements within the housing 34'; the opening defines the aperture of the image which the ophthalmoscope 120 projects to the camera 16' or other recording or observation device.

Each mask 124, 126 is mounted on the casing for rotation about a respective rotation axis; the rotation axes are parallel to the optical axis 20' of the instrument. The masks are located substantially symmetrically on either side of the aperture opening 130, and each projects into the opening over the portion of the projected fundus image which corresponds to the excessively illuminated regions 30 and 32 of FIG. 2. However, each mask 124, 126, which like the reciprocating masks of the FIG. 1 ophthalmoscope 10 is substantially optically opaque, has a selected circumferential contour. The configuration of this contour is such that, when the mask rotates, it passes to the viewer selected fractions of the image light incident on it. The level of the image light which the rotating masks thus transmit has essentially the same intensity as at the center of the image, i.e. as the uniform portion of the FIG. 2 graph between the Y-axis and the point A.

The rotating mask system does not require synchronization with the illuminating system 22' or with whatever image recording is used at the viewing point of camera 16'. In typical operation, the motor drive which rotates the masks runs continuously, the illuminating system 22' provides continuous illumination of the eye fundus being examined, and the camera or other image recording instrument is operated independent from the illumination and from the masks to provide whatever photographs or other recordings are desired of the fundus image. The reason for this time independence of the rotating mask system 122 is that the illustrated rotating masks selectively block image illumination several times during the interval of one photographic exposure or other recording interval. This relatively high speed masking is readily obtained by scalloping each mask with a pattern which repeats around the mask circumference and by rotating each mask at a sufficiently high rate of speed relative to the image recording time.

The time independence with which the ophthalmoscope 120 thus operates significantly reduces its cost relative to a system which requires synchronized operation, and simplifies construction and operation. Another advantage of the rotating system is that it operates quietly and smoothly with minimal vibration. This further enhances the quality of the images which can be recorded with the instrument.

Each rotating mask in the ophthalmoscope 120 effects the brightness of the image at the portions which correspond to the regions 30 and 32 of FIG. 2. Accordingly, each disk-like mask has a circular outer periphery 124a, 126a, along which the radially-outermost points lie, having a radius corresponding closely to the outer curvature of the FIG. 2 portion 32, i.e. the curvature of the portion edge adjacent point A. (In one embodiment of the invention, each mask as in FIG. 11 has a maximum outer diameter of twenty-two millimeters.)

Further, each mask can be mounted on the support casing 128 to project into the aperture opening 130 to locate this circular periphery 124a, 126a generally in register with this edge of the portion 32. The illustrated embodiment, however, mounts each mask on a separate slide block 125, 127 which is movably adjustable relative to the casing 128 in the manner detailed hereinafter. This enables each mask 124, 126 to be adjustably positioned for optimal masking of the eye being studied, e.g. for eyes of different geometries.

The scalloping of each rotating mask corresponds approximately to the change in image brightness as a function of radial distance, as the graph in FIG. 2 plots. The opaque area of the mask accordingly progressively increases with decreasing radius on the disk-like shape of the mask, as FIG. 11 shows. It has further been found that the mask in some instances imposes perceptible shadows on the ophthalmoscope image when, for example, many crests of the scalloped edge are at the same radial distance, and similarly when many valleys or troughs are at the same radial distance. To avoid this and other optical "imprints" of the rotating mask, the mask configuration which FIG. 11 illustrates has several peaks and valleys, and in general has an overall distribution of the scalloped edge, at different radial distances from the center of the circular outer periphery 124a, 126a. It further is considered preferable that the corners of the scalloped edge be rounded, i.e. to have gradual transitions.

Figure 12:
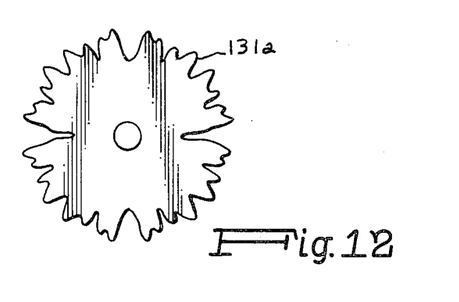
FIGS. 12 and 13 show other configurations of an optical mask for use in the ophthalmoscope of FIG. 10.

The scalloped mask configuration which FIG. 11 shows illustrates one preferred embodiment for attaining the foregoing objectives. The configuration has a pattern of narrow-wide-narrow scallops which repeats every 90° around the mask circumference. Superimposed on this are two equally-spaced narrower and significantly deeper scallops. FIG. 12 shows another mask configuration, the basic contour of which repeats every 45° so that the pattern is repeated eight times around the mask periphery. Superimposed on this repeating pattern are four equally-spaced deeper troughs, two opposite ones of which are deeper than the others. Other mask configurations can be used, the invention is not limited to those which FIGS. 11 and 12 show.

Figure 13:
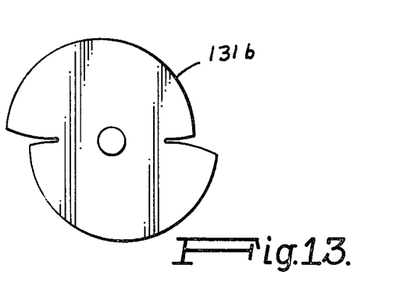

FIG. 13 shows one such alternative; that mask has a contour formed by two helically or spirally increasing semicircular segments. The narrow width of one segment is adjacent the wide end of the other, and a slot apertures the juncture. The illustrated rotating masks thus provide narrow slit-like apertures at locations corresponding to the bright fundus regions 30 (FIG. 2) and significantly more and radially-increasing aperture area at locations corresponding to the transition regions 32.

With further reference to FIGS. 10 and 11, the support casing 128 of the illustrated ophthalmoscope 120 is constructed with a plate 132 that mounts the mask system 122 as well as the lens housing 34' and the brackets 36', 36' that carry the fiber optic bundles 22a', 22b'. The plate is apertured to form the opening 130 and is recessed with channels 134, 136 that slidably seat the slide blocks 125, 127. Each channel extends laterally (i.e. horizontally, from side to side in FIGS. 10 and 11) along the plate from one edge toward the opening 130 and has upper and lower slide rails 138 extending therealong. Each block 125, 127 has slide tracks 140 along the upper and lower sides and slidably seats within one channel with the channel rails slidably engaged with the tracks. The block is thus slidable along the channel and the rail-track engagement holds the block securely seated in the channel. (Alternative to the rail and track structure, one can, for example, use a cover plate overlying and fastened to plate 132 to secure the slide blocks in the channels).

Each slide block 125, 127 carries one mask 124, 126 and carries a drive motor 142, 144 that rotates the mask by means of a drive belt 146, 148. The masks are fixed on shafts 150, 152 that are rotatably mounted, as with bearings, to the blocks 125, 127 adjacent the ends thereof proximate to the opening 130. The shafts, which are parallel to the optical axis 20' to dispose the masks in a common plane transverse to this axis, carry sheaves 154, 156. The motors 142, 144 are mounted on the blocks at locations spaced further from the opening 130; they extend outward from the casing 128 through slots which aperture the plate 132 along the channels 134, 136. The shaft of each motor extends through the motor-mounting slide block and carries a drive sheave 158, 159 which the belt 146, 148 couples to the mask sheave on that block. With this construction, sliding adjustment of a block 125, 127 along a channel adjusts the amount of mask projection into the opening 130, but does not change the coupling of the mask to its drive motor.

As FIGS. 10 and 11 also show, the casing plate 132 pivotally mounts upstanding levers 158, 160 which are pinned at slots 162, 164 to the slide blocks 125, 127 respectively. Pivotal movement of a lever by the operator slides the corresponding block, along the channel in which it is mounted, to effect this positioning adjustment of a mask. (Means not shown can be provided to secure the slide blocks after adjustment.) It will be seen that the levers are well spaced from the ophthalmoscope axis 20' and hence are readily accessible to the operator.

As indicated above, the speed of rotation of each motor 142, 144 preferably is selected so that each mask 124, 126 obscures and alternatively passes image illumination several times during the imaging interval, e.g. during the exposure time for photographing the fundus image. By way of illustrative example, an embodiment with the illustrated construction rotates each mask through at least two full revolutions during each photographic exposure of the fundus image. Where desired, the motor speed can be adjustable to enable the operator to change the speed of mask rotation.

As FIG. 10 also shows, the illustrated optical source 24' has a single lamp and two lens systems which direct illumination onto the entry facets of the fiber optic bundles 22a' and 22b'.

During operation of the ophthalmoscope 120, the optical source 24' and the motors are turned on, and the slide blocks adjusted for optimal masking of the eye being examined. The resultant fundus image can then be studied or recorded, e.g. photographed, as desired. So long as the masks rotate sufficiently fast so as not to undesirably shadow the image, there is no need to synchronize the mask rotation or the optical source operation with the image viewing and recording.

Although described with reference to an ophthalmoscope 120 which provides for adjustable lateral positioning of the masks, a rotating mask system as FIGS. 10–13 illustrate can be practiced with fixed axes of mask rotation. The masking will match some eyes, and will also provide significant, nearly equal, improvements in observed image illumination for the eyes of other subjects.

Figure 14:
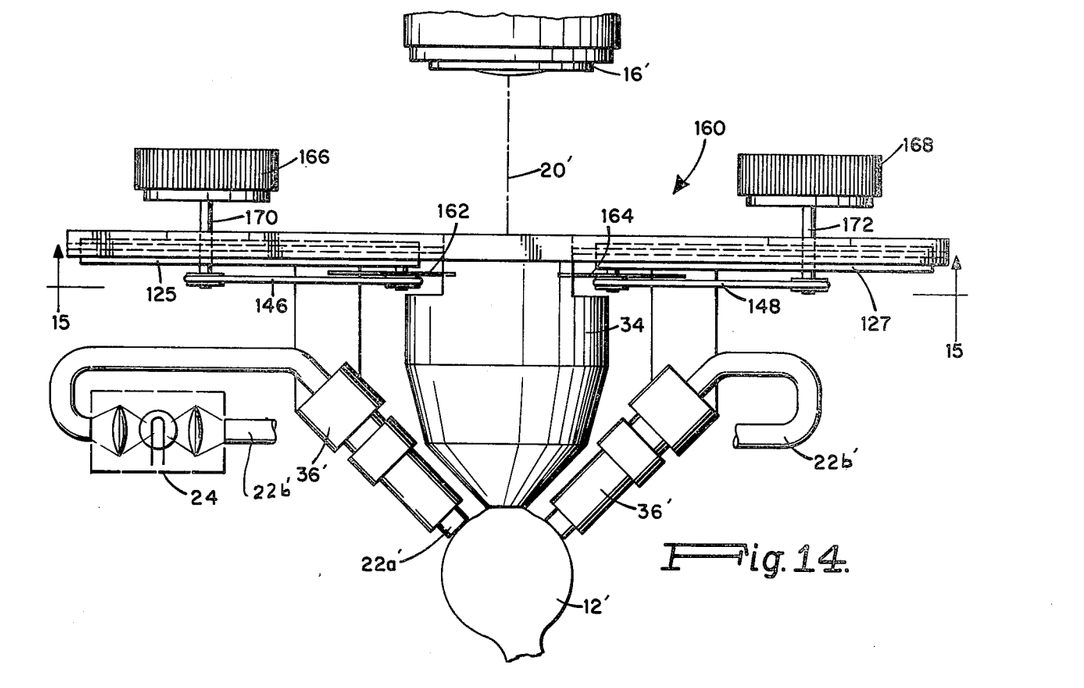
FIG. 14 is a horizontal plan view similar to FIG. 1 of a third embodiment of the invention.
Figure 15:
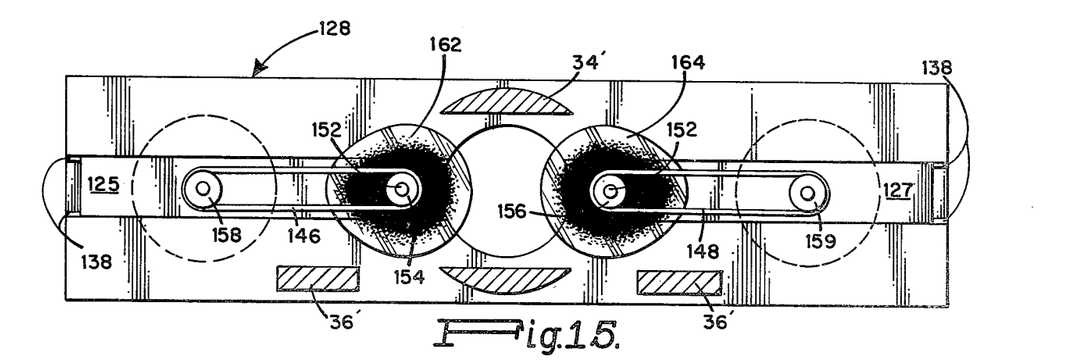
FIG. 15 is an elevation view partly broken away of the ophthalmoscope of FIG. 14 and taken along line 15—15 therein.

The invention can also be practiced with an ophthalmoscope 160, shown in FIGS. 14 and 15, which has optical masks 162, 164 that are adjustable, but which can remain stationary during the fundus examination and image recording. Further, the masks 162, 164 in this instrument have selected graduated optical transmission, as provided for example by a selectively-exposed photographic negative. The ophthalmoscope 160 is constructed in large part like the opthalmoscope 120 of FIGS. 10 and 11, except with different masks and a different mask-moving mechanism. Accordingly, elements of the ophthalmoscope 160 which are common to FIGS. 10 and 11 bear the same reference numerals in FIGS. 14 and 15.

Instead of carrying a motor as in FIGS. 10 and 11, each slide block 124, 125 of the FIG. 14 ophthalmoscope 160 carries a knob 166, 168. The knob is mounted for rotation with a shaft 170, 172 journaled to the slide block 125, 127, respectively. The shaft extends beyond the block to mount the respective drive sheave 158, 159. The knobs 166 and 168 serve both to adjustably position the mask-carrying slide blocks 125 and 127 and to rotationally adjust the masks. However, the slide blocks can, when desired, be adjustably positioned by means of pivoting levers 158 and 160 as shown in FIGS. 10 and 11, as well as with other adjustment mechanisms.

Figure 16:
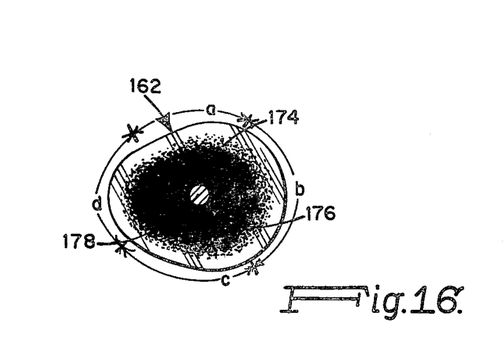
FIGS. 16 and 17 show other configurations of an optical mask for use in the ophthalmoscope of FIG. 14.

As shown in FIG. 15 and with greater detail in FIG. 16 for the mask 162, each mask 162, 164 has a central region 174 that is substantially uniformly dense at an optical density of three, and which is bounded by a transition region 178. This region has an opacity that decreases from density three to zero with increasing radius from the central point 178 about which the mask is rotated on the corresponding shaft 150, 152. The periphery of the mask is essentially transparent. The contours of the mask regions 174 and 176 correspond respectively with the contours of the overly-bright fundus image regions 30, 32 of FIG. 2. The radial change in opacity in mask region 176 corresponds inversely to the change in brightness which the curve in FIG. 2 shows, particularly between points A and B. Moreover, different circumferential portions of the graduated mask correspond to these features as found with different eyes, e.g. eyes of different geometry and of different optical transmission for illumination applied at the sclera.

For this purpose, the graduated mask shown in FIGS. 15 and 16 has four circumferentially-extending sections a, b, c and d. In each section the central region 176 is bounded by a different curvature, typically a circular curvature of different radius from the other sections. The transition region is of generally uniform width around the central region. The mask thus has a generally eliptical, egg-shaped contour of the central region 176, as well as of the transition region 178.

With this construction and arrangement of each mask, the operator of the ophthalmoscope 160 can adjust the mask in and out relative to the ophthalmoscope opening 130 (i.e. laterally in FIGS. 14 and 15), and rotationally adjust the mask, to match the mask closely with the localized increased brightness due to illumination at the sclera for the particular eye being examined. The graduated mask preferably is located out of the focal plane of the observer/recorder of the fundus image in order to diminish the appearance of a shadow of the mask.

Figure 17:
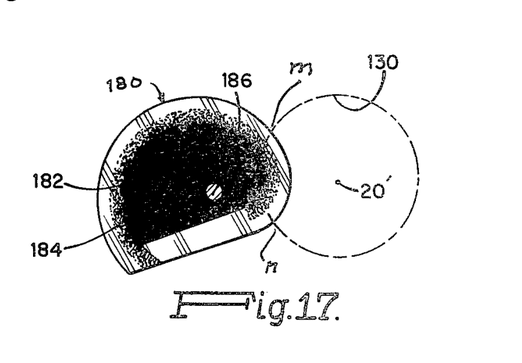

FIG. 17 shows a graduated mask 180 having a continuously changing curvature such that it can more optimally mask different eyes. The mask is adjusted by rotation and by lateral motion, and remains stationary during fundus examination, as described with reference to FIGS. 14–16. The mask 180 has a central region 182 of uniform optical density three which is bounded by a helical curve. A transition region 184 of radially-decreasing opacity from density three to zero bounds the central region and is again of uniform width; hence it follows a helical path. Further, the mask preferably is rotated about an off-center point 186 and on a rotation axis such that the points (m) and (n) at which the mask intersects the ophthalmoscope opening 130 remain substantially symmetrically located relative to the horizontal diameter of the circular opening as the mask is rotated. This arrangement is desired to maintain the area of the mask which overlaps the circle substantially equally-divided about the horizontal diameter of the opening 130. That is, the projecting portion of the mask 180 remains essentially centered on the horizontal diameter of this circular opening, as desired.

The masks of FIGS. 16 and 17, like those suitable for use in the ophthalmoscopes of FIGS. 1 and 10, are thin, flat disks. However, rather than being uniformly opaque, as is the case for the masks of FIGS. 1 and 10, the semi-transparent masks of FIGS. 16 and 17 have a graduated opacity as described; selectively exposed and developed photographic negative can provide the desired ranges of opaqueness.

The invention thus provides a masking system that produces essentially uniform brightness in the image of an eye fundus illuminated through the sclera. The masking system can be used to advantage both in fundus photography or other recordation, as well as in simple ophthalmic observations.

It will thus be seen that the objects set forth above, among those made apparent from the peceding description, are efficiently attained. Since certain changes may be made in the above construction without departing from the scope of the invention, it is intended that all matter contained in the above description or shown in the accompanying drawings be interpreted as illustrative and not in a limiting sense.

It is also to be understood that the following claims are intended to cover all the generic and specific features of the invention herein described, and all statements of the scope of the invention, which, as a matter of language, might be said to fall therebetween.

Having described the invention, what is claimed as new and secured by Letters Patent is:

1. In a device for examining an eye fundus under applied illumination, said device having
   lamp means for illuminating the fundus and
   means for imaging the fundus through the lens of the eye and along an optical axis for viewing,
   said lamp means directing light onto the sclera of the eye to illuminate the fundus,
   the improvement comprising
   optical image masking means for rendering the optical brightness of the image of the fundus more uniform as a function of location relative to the fundus than is the brightness of such illuminated light transmitted through the sclera onto the fundus.

2. In a device according to claim 1, the further improvement wherein the masking means includes at least one mask member movable to provide selective masking of image brightness.

3. In a device according to claim 1, the further improvement wherein the masking means includes a mask member having a contoured periphery and movable to interpose the contoured periphery selectively into a portion of the image of the fundus for providing selective masking of image brightness.

4. In a device according to claim 1, the further improvement wherein the masking means includes a mask member having prescribed movement in at least a portion of the image of the fundus for providing selective masking of image brightness.

5. In a device according to claim 1, the further improvement wherein the masking means includes a mask member movable in at least a portion of the image of the fundus which corresponds to a location where such illuminating light passes through the sclera.

6. In a device according to claim 1, the improvement wherein the masking means includes a mask member movable in a plane transverse to said optical axis and for selectively blocking light from a location on the fundus where such illuminating light is transmitted through the sclera.

7. In a device according to claim 6, the further improvement wherein the plane in which said mask member is movable is removed from the location at which said viewing means images the fundus.

8. In a device according to claim 2, the further improvement comprising means for providing such movement of the mask member in a plane transverse to said optical axis.

9. In a device according to claim 1, the further improvement wherein the masking means includes a mask member for projecting a selectively-graduated optical opacity.

10. In a device for examining an eye fundus under applied illumination, said device having lamp means for illuminating the fundus and a contact lens for viewing the fundus, said contact lens having an optical axis, said lamp means comprising means for directing light onto the sclera of the eye being examined for transmission through the sclera to illuminate the fundus, the improvement wherein mask means are provided for movement with respect to said optical axis, and wherein mask driving means are provided for moving said mask means, said mask means being movable for masking the image of the fundus portion most intensely illuminated by said means for directing light onto the sclera.

11. In a device according to claim 10, the further improvement wherein said light-directing means includes first and second fiber optic bundles, each of which has an exit facet for placement on an exterior surface of the eye at a region of the sclera having relatively high optical transmission to the eye fundus, and wherein said mask means comprises first and second opaque mask members each movable between a respective second position in which it masks the image of the fundus portion most intensely illuminated, and a respective first position in which it intercepts less of the light transmitted by said contact lens.

12. In a device according to claim 11, the further improvement wherein the portion of each said mask member that masks a portion of the fundus image is substantially in the shape of a segment of a circle.

13. In a device according to claim 11, the further improvement wherein a linkage is provided between said first and second mask members, thereby enabling a single mask driving means to drive both mask members simultaneously.

14. In a device according to claim 13 wherein said lamp means includes a single light source, the further improvement wherein said lamp means also includes a shuttle member that receives a light-receiving end of each said fiber optic bundle and means for moving said shuttle member between a first position in which the light-receiving end of said first fiber optic bundle is exposed to light emitted from said light source and a second position in which the light-receiving end of said second fiber optic bundle is exposed to light emitted from said light source.

15. In a device according to claim 14, the further improvement wherein said mask driving means is arranged for driving said mask means through a full cycle between said first position and said second position while each said fiber optic bundle is exposed via said shuttle member to light from said light source.

16. In a device according to claim 14, the further improvement wherein shuttle position sensor means are provided for sensing the shuttle position of the shuttle member for synchronizing the movement of said mask means relative to the movement of said shuttle member.

17. In a device according to claim 10, the further improvement wherein the movement of said mask means is a displacement transverse to said optical axis and said driving means moves said mask means between said first and second positions with a non-linear rate, thereby providing compensation for the varying intensity of light on the region of the fundus corresponding to the portion of the fundus image occluded by the mask means.

18. In a device according to claim 17, the further improvement wherein said driving means moves said mask means such that, as the mask means moves from said first position to said second position, an initial portion of the movement is at a faster rate than subsequent portions of the movement.

19. In a device according to claim 18, the further improvement wherein said mask means is driven from said second position to said first position with, an initial portion of that movement slower than subsequent portions of that movement.

20. In a device according to claim 18, the further improvement wherein said mask driving means includes a motor element driving a rotary cam member, said cam member having a curvilinear slot for receiving a cam follower that is linked to said mask means for said driving of said mask means.

21. In a device for examining an eye fundus under applied illumination, said device having lamp means for illuminating the fundus and a lens for viewing the fundus along an optical axis, said lamp means including means for directing light onto the sclera of the eye being examined for transmission through the sclera to illuminate the fundus, the improvement comprising optical masking means in optical alignment with said lens for rendering the optical brightness of the image of the fundus more uniform as a function of location relative to the fundus than is the brightness of such illuminating light transmitted through the sclera onto the fundus.

22. In a device according to claim 21, the further improvement wherein said optical masking means selectively masks the image of the fundus at a region corresponding to a location on the fundus where such illuminating light is transmitted through the sclera.

23. In a device for viewing an eye fundus under applied illumination and having lamp means for illuminating the fundus through the eye sclera and lens means for viewing the fundus through the lens of the eye and along an optical axis, the improvement comprising
optical mask means disposed in selected optical alignment with the lens means for reducing the optical intensity of the fundus image at regions of the image corresponding to locations on the fundus where illuminating light enters the eye through the sclera, thereby to diminish significant differences in the optical intensity of the fundus image at different regions thereof.

24. In a device according to claim 23, the further improvement in which said optical mask means includes at least one mask member of selected optical opaqueness within a contoured periphery.

25. In a device according to claim 24, the further improvement comprising means for mounting said mask member relative to said lens means and lamp means for selected rotation about a second axis parallel to said optical axis.

26. In a device according to claim 25, the further improvement in which said mounting means provides selected rotatable adjustment of said mask member about said second axis.

27. In a device according to claim 26, the further improvement comprising motor means for drivingly rotating said mask member about said second axis.

28. In a device according to claim 25, the further improvement comprising transverse adjustment means for adjustably positioning said mask member and thereby said second axis relative to said optical axis.

29. In a device according to claim 24, the further improvement comprising means for mounting said mask member relative to said lamp means and to said lens means for adjustable movement relative to said optical axis selectively to interpose the mask member partially over the fundus image which said lens means provides.

30. An ophthalmic instrument for viewing an eye fundus under applied illumination and having lamp means for illuminating the eye fundus through the eye sclera and lens means for viewing the fundus through the lens of the eye and along an optical axis, and further comprising
at least one optical mask member disposed in selected optical alignment with said lens means and with said optical axis and movable relative to said optical axis for reducing the optical intensity of the fundus image from said lens means at at least one region of the image corresponding to at least one location on the fundus where light enters the eye through the sclera.

31. An instrument as defined in claim 30, further comprising means mounting said mask member relative to said lens means and said lamp means substantially in a plane transverse to said optical axis and for movement substantially within said plane.

32. Apparatus as defined in claim 30 in which said mask member includes an optically-opaque disk-like element having a selectively-contoured periphery.

33. In a device according to claim 32, the further improvement in which said opaque mask element has a peripheral contour comprising regions of different roundnesses.

34. A device according to claim 32 in which said opaque mask element has a contoured periphery comprising regions of different curvatures corresponding generally to the curvatures of different eyes.

35. A device according to claim 30 in which said mask member has a first central region of significant optical opacity and bordered by a second region of lesser optical opacity, said different opacities of said mask member being selected for imparting a substantially uniform level of optical brightness to the fundus image at the image region corresponding to the fundus location where light enters through the sclera.

36. A method for ophthalmic examination of an eye fundus under illumination applied at least in part through the eye sclera, said method comprising the improvement of optically masking the image of the eye fundus at the image region corresponding to the fundus location where the applied illumination enters through the sclera, for imparting a substantially uniform level of optical brightness to the fundus image including at the aforesaid region.

37. A method as defined in claim 36 in which said masking step includes the further step of adjusting the masking in accordance with parameters of the eye being examined.

38. A method as defined in claim 36 in which said masking step includes the step of selectively applying said optical masking for diminishing the visibility in the fundus image of the means for introducing said optical masking.

* * * * *

UNITED STATES PATENT AND TRADEMARK OFFICE
CERTIFICATE OF CORRECTION

PATENT NO. : 4,200,362
DATED : April 29, 1980
INVENTOR(S) : Oleg Pomerantzeff

It is certified that error appears in the above-identified patent and that said Letters Patent are hereby corrected as shown below:

Column 2, line 58, change "fact" to --face--.

Column 9, line 5, change "Silmultaneous" to --Simultaneous--.

Signed and Sealed this

Sixth Day of January 1981

[SEAL]

Attest:

SIDNEY A. DIAMOND

Attesting Officer

Commissioner of Patents and Trademarks